United States Patent [19]

Williams

[11] Patent Number: 4,894,172

[45] Date of Patent: Jan. 16, 1990

[54] PROCESS FOR PROGRAMMING OF FIELD-FLOW FRANCTIONATION

[75] Inventor: Philip S. Williams, Salt Lake City, Utah

[73] Assignee: University of Utah, Salt Lake City, Utah

[21] Appl. No.: 237,188

[22] Filed: Aug. 29, 1988

[51] Int. Cl.[4] ............................................. B03B 5/00
[52] U.S. Cl. ...................................... 210/748; 209/1; 209/155; 210/788; 210/802
[58] Field of Search ................ 209/127.1 R, 129, 131, 209/155, 130; 210/101, 198.2, 511, 512.1, 512.3, 658, 748, 787, 788, 775, 801, 802; 494/27, 37, 41, 43, 85; 204/186, 182.7

[56] References Cited

U.S. PATENT DOCUMENTS

| | | | |
|---|---|---|---|
| 3,449,938 | 6/1969 | Giddings | 210/775 |
| 4,147,621 | 4/1979 | Giddings | 210/646 |
| 4,214,981 | 7/1980 | Giddings | 209/155 |
| 4,250,026 | 2/1981 | Giddings et al. | 209/155 |
| 4,284,498 | 8/1981 | Grant et al. | 209/155 |
| 4,285,810 | 8/1981 | Kirkland et al. | 494/37 |
| 4,623,470 | 11/1986 | Adler | 210/512.3 |
| 4,657,676 | 4/1987 | Keary et al. | 210/198.2 |
| 4,726,904 | 2/1988 | Ayers | 210/658 |
| 4,737,268 | 4/1988 | Giddings | 210/748 |
| 4,830,756 | 5/1989 | Giddings | 210/748 |

OTHER PUBLICATIONS

Int. Patent Publication WO87/07532, 17 Dec. 87, Whitlock.
Yang et al, Anal. Chem., 1974, 46, 1924.
Giddings et al., Anal. Chem., 1976, 48, 1587.
Kirkland et al., Anal. Chem., 1980, 52, 1944.
Yau and Kirkland, Sep. Sci. Technol., 1981, 16, 577.
Kirkland, Rementer and Yau, Anal. Chem., 1981, 53, 1730.
Giddings et al., Anal. Chem., 1987, 59, 28.
Williams and Giddings, Anal. Chem., 1987, 59, 2038.

Primary Examiner—Richard V. Fisher
Assistant Examiner—Joseph Drodge

[57] ABSTRACT

A process for programming of field decay or of increase of channel flow in field-flow fractionation which imparts improved uniformity of fractionating power which comprises an improvement in the field-flow fractionation technique which involves varying one of the parameters that affect the interaction of the sample components with the field and fluid medium in order to reduce separation time and better equalize component separation. These parameters include decreasing the field strength according to a specific power equation, or increasing the flow rate according to another power equation, or use of both parameters together.

9 Claims, 5 Drawing Sheets

PROCESS FOR PROGRAMMING OF FIELD-FLOW FRANCTIONATION

BACKGROUND OF THE INVENTION

1. Field of the Invention

This invention relates to field-flow fractionation, a technique used for separation and characterization of complex polymeric, macromolecular and particulate materials. More particularly, the invention relates to a new technique for programming both field and flow in field-flow fractionation.

Specifically, the invention provides a new technique for programming of field decay or of increase of channel flow in field-flow fractionation, which I call power programming, which imparts improved uniformity of fractionating power. The new process comprises an improvement in programming a field-flow fractionation wherein a carrier fluid containing particles or macromolecules to be separated is forced through a thin flow-channel and a field or gradient is used to induce a driving force acting across the thin dimension perpendicular to the fluid axis, said improvement involves varying one of the parameters that affect the interaction of the sample components with the field and fluid medium in order to reduce separation time and better equalize component separation, said parameters including decreasing the field strength according to the power equation set out below, or increasing the flow rate according to the other equation set out below, or use of both parameters together.

The improvement involving the variation of the field strength comprises holding the field strength S constant at an initial level $S_0$ for a time-lag period of $t_1$, and then decaying the field strength with time t according to the equation $$S = S_0 \left[ \frac{t_1 - t_a}{t - t_a} \right]^p$$

with the requirements that $t \geq t_1 > t_a$, $t_1 \geq 0$ and $p > 0$, and where S is the field strength at time t, $S_0$ is the initial field strength, and $t_1$ is a time lag following the start of elution through the field-flow fractionation (FFF) system during which the field is held constant at $S_0$. The remaining time parameter $t_a$ and the power p take particular optimum values when highly polydisperse materials are to be characterized, generally with $t_a = -p\, t_1$ and $t_1 \neq 0$.

The improvement involving the variation of the mean flow velocity utilizes a program taking the form.

$$<V> = <V>_0 \left[ \frac{t_2 - t_b}{t - t_b} \right]^q$$

wherein $t \geq t_2 > t_b$, $t_2 \geq 0$ and $q < 0$ for a programmed increase in flow velocity, and where $<v>$ is the mean channel flow velocity at time t, $<v>_0$ is the initial mean flow velocity and $t_2$ is a time lag during which $<v>$ is held constant at $<v>_0$. The remaining time parameter $t_b$ and the power q will take, as with the power programmed field operation, values consistent with lessened variation of fractionating power over wide particle size or molecular weight range, generally with $t_b = q\, t_2$ and $t_2 \neq 0$.

The invention also provides a process involving the power programming of both the field and flow velocity simultaneously to provide advantages not obtainable when programming either the field or flow alone.

2. Prior Art

There is a growing need in industry and health sciences for the separation of submicron particles including latices, environmental particles, carbon black, industrial powders, crystallization products, and related particulate matter.

Various methods have been proposed, but in general, they have been slow, too low in throughput, inefficient, expensive or have failed to effect the separation with the desired degree of resolution needed for commercial operations.

Some of the highest resolution techniques disclosed have been those based on field-flow fractionation as disclosed in U.S. Pat. No. 3,449,938 and U.S. Pat. No. 4,147,621, but their resolution leaves much to be desired. For example, the technique is often impractical because of the inordinate time required for elution of the larger particles. For example, when the technique is used to fractionate wide-ranging mixtures problems are encountered due to the incomplete resolution of early peaks and the excessive retention time and peak width of late peaks.

The solution to the above problem is often effectively realized in various programming techniques. For example, various retention-influencing parameters, such as temperature, solvent properties, field strength, flow velocity, etc. are varied in the course of a run in order to expose in an orderly sequence each of the components to effective separation conditions.

Field programming has been most extensively developed. In this technique the field strength is reduced with time, gradually according to some specific mathematical function. Parabolic field decay (linear rpm decay) and parabolic decay combined with an abrupt reduction of field strength were used in the earliest programmed sedimentation FFF experiments (Yang et al., Anal. Chem. 1974 46, 1924). Linear and parabolic field decay combined with an initial time lag period were utilized for thermal FFF (Giddings et al., Anal. Chem. 1976 48, 1587). Subsequently, Kirkland, Yau, and co-workers introduced a widely applied exponential field decay with and without time lag (Kirkland et al., Anal. Chem. 1980 52, 1944).

These proposed programming techniques, however, have various limitations which have restricted their ability to fractionate particulate, polymeric and macromolecular samples uniformly. For example, with the exponential decay program there is a great variation of fractionating power with either particle diameter or molecular weight. The limitations of these prior known techniques are illustrated in the comparative data presented hereinafter.

It is an object of the invention, therefore, to provide a new technique for the programming of field strength and channel flow in field-flow fractionation. It is a further object to provide a programming technique which gives improved uniformity of fractionating power over a substantial particle diameter or molecular weight range. It is a further object to provide a new mathematical form for field decay which, with the proper adjustment of parameters, yields uniform plots of fractionating power vs particle diameter or vs molecular weight. It is a further object to provide a programming technique which gives shorter analysis time at some required minimum fractionating power with a broader range of particle size or molecular weight than is obtainable with previously proposed techniques. It is a further object to provide a new programming technique for FFF which involves programming of field strength, channel flow velocity as well as a combination of both. These and other objects of the invention will be apparent from the following detailed description thereof.

SUMMARY OF THE INVENTION

It has now been discovered that these and other objects can be accomplished by the new process of the invention which presents for the first time an efficient process for programming field-flow fractionation to yield a greatly improved uniformity of fractionating power.

The new process comprises an improvement in programming of field-flow fractionation wherein a carrier fluid containing particles or macromolecules to be separated is forced through a thin flow channel and a field or gradient is used to induce a driving force acting across the thin dimension perpendicular to the fluid axis, said improvement involves varying one or more of the parameters that affect the interaction of the sample components with the field and fluid medium to reduce analysis time and better equalize component separation, said parameters including decreasing the field strength according to the power equation set out below, or increasing the channel flow rate according to the other power equation set out below.

The improvement involving the variation of the field strength comprises holding the field strength S constant at an initial level $S_0$ for a time-lag period of $t_1$, and then decaying the field strength with time t according to the equation $$S = S_0 \left[ \frac{t_1 - t_a}{t - t_a} \right]^p$$

with the requirements that $t \geq t_1 > t_a$, $t_1 \geq 0$, and $p > 0$, and where S is the field strength at time t, $S_0$ is the initial field strength, and $t_1$ is a time lag following the start of elution through the FFF system during which the field is held constant at $S_0$. The remaining time parameter $t_a$ and the power p take particular optimum values when highly polydisperse materials are to be characterized, generally with $t_a = -p\, t_1$ and $t_1 \neq 0$. For sedimentation and flow FFF, in the limit of high retention and in the absence of steric interference, hydrodynamic lift forces, etc., $F_d$ may be shown to be dependent on d raised to the power $\{3n/[2(1+p)]\} - (1/2)$ where n is equal to 3 for sedimentation FFF and 1 for flow FFF. For thermal FFF, again for high retention and in the absence of non-idealities, entropic lift forces, etc., the mass based fractionating power $F_M$ varies approximately with the normal diffusion coefficient D (at the temperature of the cold wall) raised to the power $(p-2)/[2(1+p)]$. Flow FFF gives the same power dependence of $F_M$ and D as thermal FFF. In all cases it may be arranged, through choice of an appropriate value for p, that fractionating power be maintained at a constant level for significantly retained components.

The improvement involving the variation of the flow rate utilizes a program taking the form $$<V> = <V>_0 \left[ \frac{t_2 - t_b}{t - t_b} \right]^q$$

wherein $t \geq t_2 > t_b$, $t_2 \geq 0$ and $q < 0$ for a programmed increase in flow velocity, and where $<v>$ is the mean channel flow velocity at time t, $<v>_0$ is the initial mean flow velocity and $t_2$ is a time lag during which $<v>$ is held constant at $<v>_0$. The remaining time parameter $t_b$ and the power q will take, as with the power programmed field operation, values consistent with lessened variation of fractionating power over wide particle size or molecular weight range, generally with $t_b = q\, t_2$ and $t_2 \neq 0$. For sedimentation and flow FFF, in the limit of high retention and in the absence of steric interference, hydrodynamic lift forces, etc., $F_d$ may be shown to be dependent on d raised to the power $\{(3-2q)n/[2(1-q)]\} - (1/2)$ where n is equal to 3 for sedimentation FFF and 1 for flow FFF. For thermal FFF, again for high retention and in the absence of non-idealities, entropic lift forces, etc., $F_M$ varies approximately with diffusion coefficient D raised to the power $(q-2)/[2(1-q)]$. Flow FFF gives the same power dependence of $F_M$ on D as thermal FFF. By increasing the flow velocity according to a power program the power dependence of $F_d$ on d may be reduced from 4 (constant field and flow operation) towards a minimum of 2.5 for sedimentation FFF, and from 1 towards a minimum of 0.5 for flow FFF, and the power dependence of $F_M$ on diffusion coefficient D (at the temperature of the cold wall) from approximately $-1$ towards $-0.5$ for thermal FFF and flow FFF.

As a further embodiment, the invention provides a process for involving the power program of both the field and flow velocity simultaneously to provide advantages not obtainable when programming either one alone. When simultaneous programming of both field and flow is carried out there will be a range of power values for each program consistent with near constant fractionating power. The two powers will be related, the relationship being dependent on the FF subtechnique. Suppose we consider the special case where $t_2$ is set equal to $t_1$ and $t_b$ is set equal $t_a$, then the ratio of S to $<v>$ would itself follow the power program described by $$\frac{S}{<V>} = \frac{S_0}{<V>_0} \left[ \frac{t_1 - t_a}{t - t_a} \right]^{p-q}$$

wherein $t \geq t_1 > t_a$, $t_1 \geq 0$ and $(p-q) > 0$. Generally, for optimum uniformity of fractionating power $t_a = (q-p)t_1$ and $t_1 \neq 0$. For sedimentation and flow FFF in the limit of high retention and in the absence of steric interference, hydrodynamic lift forces, etc., Fd may be shown to be dependent on d raised to the power $\{(3-2q)n/[2(1+p-q)]\} - (1/2)$ where n is equal to 3 for sedimentation FFF and 1 for flow FFF. For thermal FFF, again in the limit of high retention and in the absence of non-idealities, entropic lift forces, etc., $F_M$ varies approximately with diffusion coefficient D (at the temperature of the cold wall) raised to the power $(p+q-2)/[2(1+p-q)]$. Again, flow FFF gives the same power dependence of $F_M$ on D as thermal FFF. Therefore $F_d$ may be maintained at a constant level when $(p+5q) = 8$ in sedimentation FFF, and when (p+q)=2 in flow FFF; $F_M$ may be held approximately constant when (p+q)=2 in both thermal and flow FFF. Furthermore, it may be shown that simultaneous power programming of the channel flow velocity (with q<0) and field strength (with p>0) is advantageous with respect to obtaining shorter analysis times at some minimum required fractionating power. Analysis time may be reduced with no effect on the constant level of fractionating power at high retention.

It has been found that the above-described new processes solve many of the defects of the prior known techniques and present for the first time highly efficient processes for the fractionation of particulate, polymeric and macromolecular samples. The new techniques are rapid and efficient and provide programming processes which give improved uniformity of fractionating power over substantial particle diameter or molecular weight range.

The process of the present invention is referred to herein as involving "power" programming due to the decay dependence on a function of time raised to a particular power.

Herein the separating ability of a system is described by the expression "fractionating power", a parameter proposed by Giddings et al., Anal. Chem. 1987 59, 28, and so much of that disclosure pertinent to the present invention is incorporated herein by reference.

For particulate samples, the particle diameter based fractionating power, $F_d$, is defined as the resolution for two closely eluting components divided by their relative difference in diameter, i.e., $$F_d = \lim_{\delta d \to 0} \frac{R_s}{\delta d/d} = \lim_{\delta d \to 0} \frac{d}{4\sigma_t} \frac{\delta t_r}{\delta d}$$

where $R_s$ is the resolution for the components differing by $\delta d$ in diameter and having a mean diameter $d$, $\sigma_t$ is the mean standard deviation in elution time of the components and $\delta t_r$ is their difference in elution time. In the limit of $\delta d \to 0$ we have $$F_d = \frac{d}{4\sigma_t} \frac{dt_r}{dd}$$

where $dt_r/dd$ is the differential of elution time with respect to d. Fractionating power is therefore uniquely defined at all diameters. A mass based fractionating power is similarly defined for separation of polymers and other macromolecules in solution.

The great advantage of the power program over, for example, time-delayed exponential field decay described by $$S = S_0 \exp(-(t-t_1)\tau')$$

where again S is the field strength at time t, $S_0$ is the initial field strength, $\tau'$ is the field decay constant and $t_1$ is a time lag before decay, generally set equal to $\tau'$ for time-delayed exponential programming as described by Yau and Kirkland (Sep. Sci. Technol. 1981 16, 577) and by Kirkland, Rementer and Yau (Anal. Chem. 1981 53, 1730), lies in the fact that program parameters may be selected such that effectively constant fractionating power is obtained over relatively wide ranges of particle size or molecular weight. Such behavior is impossible to achieve with exponential field decay. It has been shown by Giddings et al., Anal. Chem. 1987 59, 28, for example that $F_d$ in exponentially programmed sedimentation field decay must ultimately fall with the reciprocal of the square root of particle diameter. $F_d$ behavior for exponential field decay is typified by a rapid increase in $F_d$ at some relatively small particle size dependent on the initial field strength, passage through a maximum at some point and then asymptotic approach to the monotonic decay described above.

On the other hand, it has been shown by Williams and Giddings, Anal. Chem. 1987 59, 2038, that for power programming of field strength in sedimentation FFF when the power p is set to 8 and $t_a$ is set to $-8t_1$, fractionating power $F_d$ rapidly increases at some relatively small particle size but then maintains an effectively constant level until particles are so large that steric interferences occur. For highly polydisperse samples this corresponds to ideal behavior where all components are equally well separated from one another and analysis time is not needlessly wasted in separating a limited region of the sample to a greater than necessary degree. For field programming in both thermal FFF and flow FFF a power of around 2 is required for constant fractionating power $F_d$ and a $t_a$ of $-2t_1$ is preferable.

Of course we need not restrict ourselves only to those conditions resulting in constant fractionating power. Special requirements may demand steadily increasing or decreasing fractionating power which may be realized through lowering or raising the power p, respectively. Note that p need not be integer. The onset of the effects of steric exclusion results in a steadily increasing $F_d$, over that predicted for normal FFF. Fractionating power falls to zero at the point of steric inversion but to a certain extent the predicted increase in $F_d$ may be compensated for by raising the power p somewhat.

Figure 3:
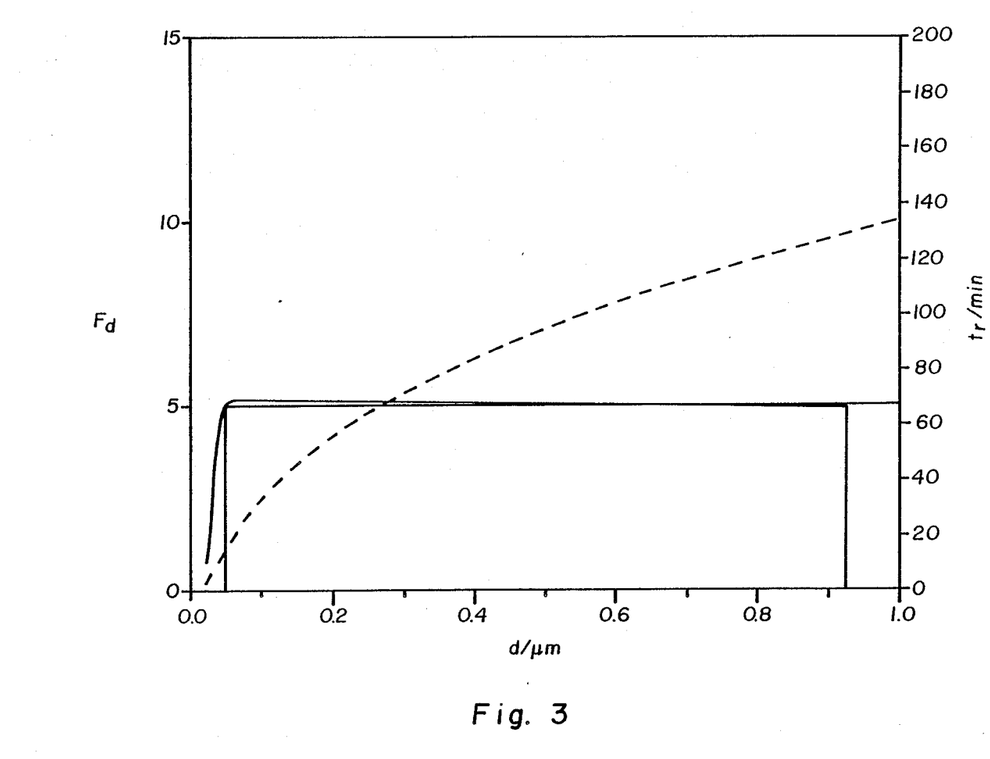
FIG. 3 is a graph illustrating the uniformity of the fractionating power of the present process.
Figure 4:
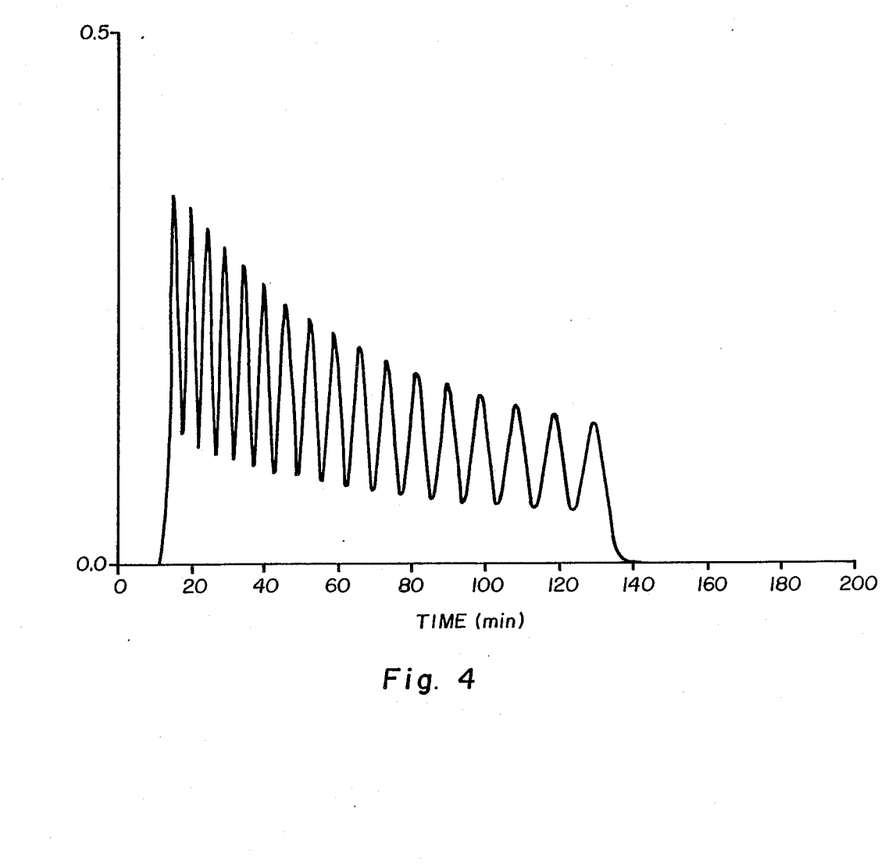
FIG. 4 is a graph showing the separation obtained by the process of the present invention.

To illustrate the fundamental differences between power programming and the time-delayed exponential programming of Kirkland and Yau where $t_1$ is set equal to the field decay constant $\tau'$, consider the following example. A mixture contains 17 monodisperse particulate components, increasing incrementally by 20% in diameter from 0.05 μm to 0.924 μm. The FFF channel has a thickness of 0.0254 cm, the density difference between the particles and the carrier fluid is 1.5 g/ml, the carrier fluid has a viscosity of 0.01 poise and the temperature of the system is 298K. The flow rate corresponds to a void time $t^0$ of 100 seconds. A resolution of unity is required between successive components, i.e., a fractionating power of around 5 is indicated across the particle size range. For power programming, the appropriate values for $(t_1-t_a)/t^0$ is calculated using Equation (57) of Williams and Giddings, Anal. Chem. 1987 59, 2038 to be 37.07. With $t_a$ set to $-8t_1$ and a $t^0$ of 100 seconds we have a $t_1$ of 412 seconds and a $t_a$ of $-3295$ seconds, together with a power p of 8 for constant $F_d$. The predicted $F_d$ as a function of particle diameter d is shown in FIG. 3 where the dotted curve represents elution time as a function of d. The rectangle included in the figure shows the limits of required $F_d$. If the predicted $F_d$ curve does not encroach on this rectangle then the requirements for the separation will have been met. The initial field strength of 1200 gravities is selected to fulfill this condition. The resulting separation for these conditions is shown in FIG. 4, the last component being eluted within 140 minutes.

Figure 5:
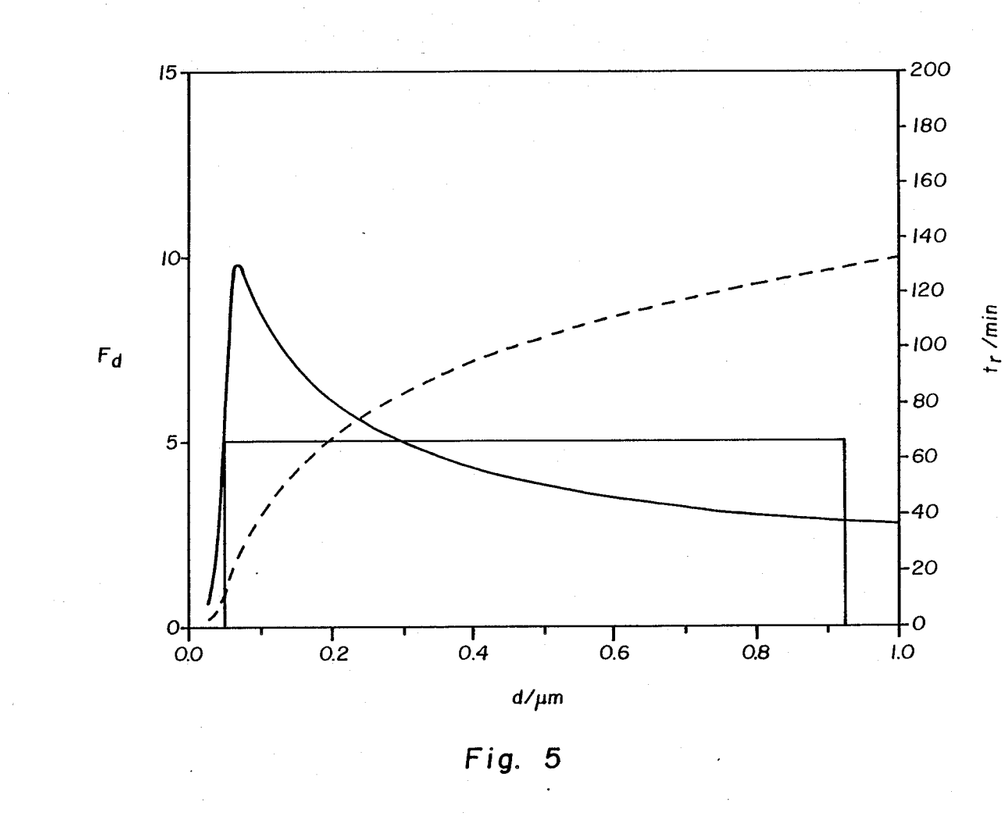
FIG. 5 is a graph showing the non-uniformity of the fractionating power of the time-delayed exponential programming.
Figure 6:
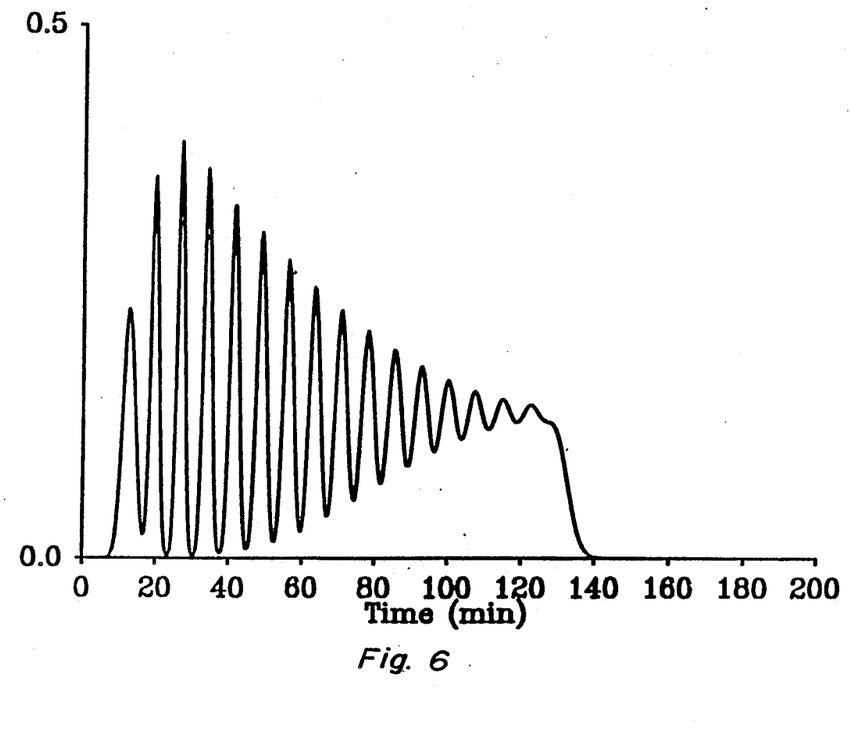
FIG. 6 is a graph showing the great variation in the separation obtained by the time-delayed exponential programming.

With the restriction that the analysis be complete in the same time as the power programmed run FIG. 5 shows a predicted $F_d$ curve for exponential programming. In order to obtain an $F_d$ of 5 at d=0.05 μm an initial field strength of 721 gravities with $t_1$ of at least 715 seconds is necessary (see Giddings et al. Anal. Chem. 1987 59, 28). A value of 803 seconds for both $t_1$ and $\tau'$ results in an analysis complete in around 140 minutes. The separation is shown in FIG. 6 where it is seen that the smaller components are separated to a greater extent than required whereas the larger components are resolved to a much lesser extent. This is perfectly consistent with the $F_d$ curve of FIG. 5 where fractionating power for particles larger than about 0.3 μm in diameter are predicted to be less well separated than desired. Conditions could of course be adjusted for time-delayed exponential programming such that $F_d \geq 5$ for the range of particle size in the mixture. This would be obtained at the expense of increased analysis time however; analysis would be complete in around 190 minutes, considerably more than the 140 minute run with power programming.

The above example demonstrates the advantages of the power program over the time-delayed exponential program when the sample to be analyzed is highly polydisperse. The power program is clearly the program of choice in these situations. Analysis of such samples at some minimum fractionating power may be obtained with considerably reduced run time by employing a power programmed field decay.

DESCRIPTION OF THE DRAWINGS

The various objects and features of the present invention will be more fully understood by reference to the accompanying drawings.

FIGS. 3, 4, 5 and 6 are to illustrate the fundamental differences between the power programming process of the present invention and the prior known time-delayed exponential programming of Kirkland et al.

DETAILED DESCRIPTION OF THE DRAWINGS

Figure 1:
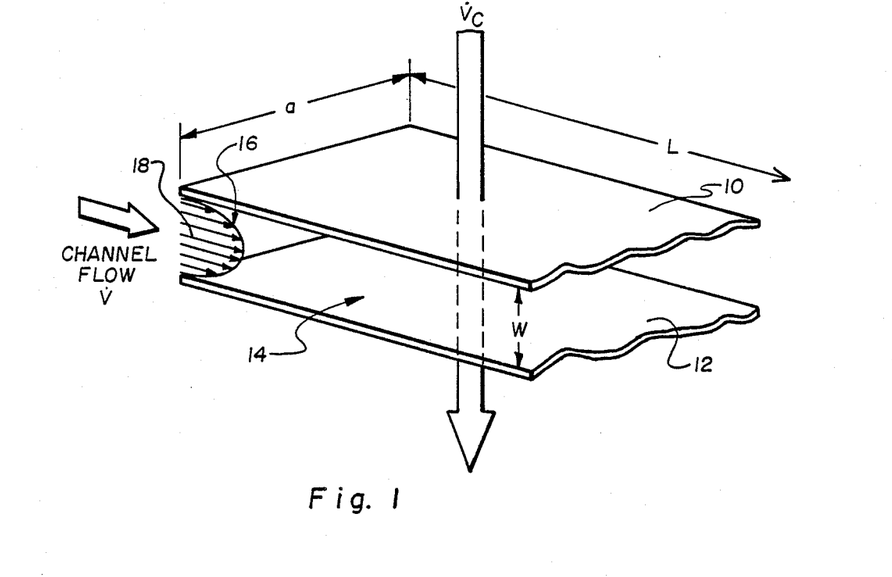
FIG. 1 is a partial cutaway, perspective view of a flow channel.

Referring to FIG. 1, the basic concept of flow FFF (an example subtechnique) is represented by the flow vectors V and $V_c$. These vectors are drawn in relation to two, closely spaced, parallel plate means 10 and 12. The region between these two plates is identified as a flow channel 14, through which fluid flow is represented by a channel profile 16 which shows relative fluid movement by means of channel flow vector 18, with the average channel flow represented by a single flow vector V, a is the width, L is the length and w is the thickness of the channel.

A cross field is imposed normal to channel flow for the purpose of causing solute migration therein. This cross flow, illustrated as $V_c$, is oriented perpendicular to the channel flow V and the respective plate means.

Figure 2:
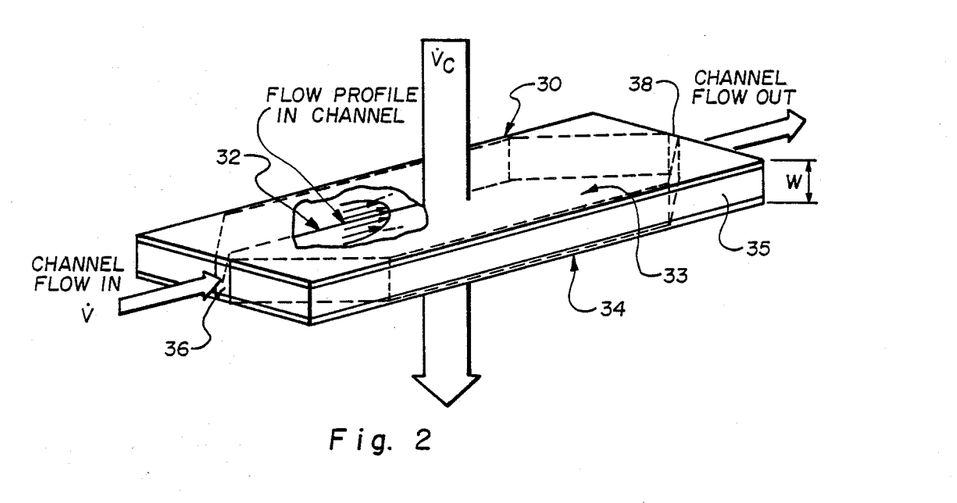
FIG. 2 depicts a flow FFF channel with enclosed structure around the channel.

The structure can be implemented by many variations of basic elements as shown in FIG. 2. The flow channel 32 is substantially defined by a first and second semi-permeable plate means, 33 and 34. Side wall structure 30 and 35 provide the respective plate means to fully enclose the chamber region 32. Since no flow should occur through the side walls, this must be of nonporous material. A general configuration might comprise a spacer plate 35, having the desired thickness interposed between the respective semi-permeable plates, the combination being tightly clamped together.

Inlet means 36 and outlet means 38 are provided at opposite ends of the chamber to enable channel flow there between. Control means associated therewith would be desirable to facilitate adjustment of V. Typically, the outlet end will feed effluent to detection means for obtaining separation results.

The graph in FIG. 3 shows the fractionating power $F_d$ plotted against the particle size diameter up to 1.0 μm, with the time being shown by the dotted line. The conditions for obtaining the plots have been presented above.

The graph in FIG. 4 shows the detector response plotted against time to show the resolution obtained by the process of the present invention.

The graph in FIG. 5 shows the fractionating power $F_d$ plotted against the particle size diameter with the time of analysis being held the same as in FIG. 3. The non-uniformity of the exponential process is clearly shown.

The graph in FIG. 6 shows the resolution obtained by the exponential process wherein the smaller components are separated to a greater extent than required whereas the larger components are resolved to a much lesser extent.

DETAILED DESCRIPTION OF THE PROCESS

Power programming of either field strength or channel flow velocity or power programming of the two system parameters simultaneously can be carried out with all subtechniques of FFF and in normal, steric and hyperlayer modes of operation. Macromolecular weight can range from $10^3$ to $10^9$ Daltons, and particle diameter from 0.001 μm to 1 μm in the the normal mode and from about 1 μm to 100 μm in the steric and steric/hyperlayer mode. Particles can vary as to density and shape.

The carrier fluid in which the particles or macromolecules are to be separated may also vary over a wide range of properties. In most cases, the fluid will be that in which the particles or macromolecules are normally prepared or contained, such as aqueous buffers for biological materials. In other cases, the carrier consists of specially prepared fluids or solutions in which the density, pH or other fluid characteristic is controlled in order to optimize the separation.

The concentration of the suspended particles or macromolecules in the initial sample fluid can also vary from extreme dilution to about 20% or more. In most cases, the concentration will vary from about 0.1% to about 5% by weight.

The rate of introducing the fluids may vary over a wide range. In general, the rate of introduction of the streams will vary from about 0.1 ml/min to about 100 ml/min.

The temperature employed in the separation process may vary over a wide range, but generally will range between about 0° C. to 25° C. Thermal FFF is a special case where the transverse driving force is due to a temperature drop maintained across the channel thickness. The temperature extremes are limited only by the necessity that the carrier fluid not change phase near either wall.

The transverse driving force or gradient used in the process of the invention are singly or in combination forces or gradients which effect transverse movement of particles at different rates, or effect movement to different transverse equilibrium or quasi-equilibrium positions. A component of each force or gradient utilized is applied perpendicular to the plane of the stream flow, i.e. along the transverse axis. The forces and gradients include, among others, sedimentation forces, such as caused by gravitation and centrifugation, electrical, dielectrical, cross flow, thermal gradient, density gradient, concentration gradients and the like. Combination of one or more forces or gradients can be used as desired or needed. Preferred forces include sedimentation forces such as gravitation and centrifugation, thermal and cross flow gradients.

The strength of the field and channel flow rate are determined by conventional means and are varied according to the formulations set out above.

The particle fractions obtained by the above-noted process will be recovered at the desired outlet means in the form of fluid solutions or suspensions, which may be used directly as such or which may be subjected to further separation means, such as centrifugation or evaporation, to recover the particles or macromolecular materials themselves.

The apparatus to be used in the process of the invention may be constructed in a variety of ways with a variety of different materials and sizes as long as it provides the channel of the necessary thickness, the desired driving force and means for controlling the strength of the force as well as timing means for controlling the field decay and increase of flow programs described herein.

Examples of various apparatus devices that can be used in the process of the invention are set out in U.S. Pat. No. 3,449,938 and U.S. Pat. No. 4,147,621.

I claim as my invention:

1. In a field-flow fractionation process wherein a carrier fluid containing a small particulate, polymeric or macromolecular sample to be separated is forced through a thin flow channel with the carrier fluid flowing in the direction of the flow axis with flow velocity and a field force or gradient is used to induce a driving force acting across the thin channel perpendicular to the flow axis, the improvement comprising holding the field strength S of the field force constant at an initial level $S_o$ for a time lag period $t_1$, and then decaying the field strength with time t according to the equation $$S = S_0 \left[ \frac{t_1 - t_a}{t - t_a} \right]^p$$

where $t \geq t_1 > t_a$, $t_1 \geq 0$ and $p > 0$, and holding the mean channel flow velocity $<v>$ constant at an initial level $<v>_o$ for a time-lag period $t_2$ and then increasing the flow velocity with time t according to the equation $$<V> = <V>_0 \left[ \frac{t_2 - t_b}{t - t_b} \right]^q$$

wherein $t \geq t_2 > t_b$, $t_2 \geq 0$ and $q < 0$, with the above symbols representing the following S = field strength
$S_o$ = field strength at initial constant level
$t_1$ = time lag period which is time for field strength held constant
t = time for decaying field strength
$t_a$ = remaining time parameter when decaying field strength
p = number of power when decaying field strength
$<v>$ = mean flow velocity
$<v>_o$ = initial mean flow velocity
$t_2$ = time lag period which is time for holding flow velocity constant
$t_b$ = remaining time parameter with increasing flow velocity
q = number of power when increasing flow velocity.

2. A process for sedimentation field-flow fractionation as in claim 1 with p and q such that $(p+5q)=8$ and $t_a=(q-p)t_1$.

3. A process for flow FFF as in claim 1 wherein p and q are such that $(p+q)=2$ and $t_a=(q-p)t_1$.

4. A process for thermal FFF as in claim 1 wherein p and q are such that $(p+q)=2$ and $t_a=(q-p)t_1$.

5. In a field-flow fractionation process wherein a carrier fluid containing a small particulate, polymeric or macromolecular sample to be separated is forced through a thin flow channel with the carrier fluid flowing in the direction of the flow axis and a field force or gradient is used to induce a driving force acting across the thin channel perpendicular to the flow axis, the improvement comprising holding the field strength S of the field force constant at an initial level $S_o$ for a time-lag period $t_1$, and then decaying the field strength with time t according to the equation $$S = S_0 \left[ \frac{t_1 - t_a}{t - t_a} \right]^p$$

wherein $t \geq t_1 > t_a$, $t_1 \geq 0$ and $p > 0$, and holding the mean channel flow velocity $<v>$ constant, with the above symbols representing the following S = field strength
$S_o$ = field strength at initial constant level
$t_1$ = time lag period which is time for field strength held constant
t = time for decaying field strength
$t_a$ = remaining time parameter
p = number of power when decaying field strength
$<v>$ = mean channel flow velocity.

6. A process for sedimentation field-flow fractionation as in claim 2 wherein p=8 and $t_a$ is $-8t_1$.

7. A process for flow FFF as in claim 2 wherein p=2 and $t_a=-2t_1$.

8. A process for thermal field-flow fractionation as in claim 2 where p=2 and $t_a=-2t_1$.

9. In a field-flow fractionation process wherein a carrier fluid containing a small particulate, polymeric or macromolecular sample to be separated is forced through a thin flow channel with the carrier fluid flowing in the direction of the flow axis with flow velocity and a field force or gradient is used to induce a driving force acting across the thin channel perpendicular to the flow axis, the improvement comprising holding the mean channel flow velocity $<v>$ constant at an initial level $<v>_o$ for a time-lag period $t_2$ amd then increasing the velocity with time t according to the equation $$<V> = <V>_0 \left[ \frac{t_2 - t_b}{t - t_b} \right]^q$$

wherein $t \geq t_2 > t_b$, $t_2 \geq 0$ and $q < 0$, and holding the field strength S constant, with the above symbols representing the following S = field strength
$<v>$ = mean flow velocity
$<v>_o$ = initial mean flow velocity
$t_2$ = time lag when holding flow velocity constant
t = time for increasing flow velocity
$t_b$ = remaining time parameter with increasing flow velocity
q = number of power when increasing flow velocity.

* * * * *